United States Patent [19]

Zinnen

[11] Patent Number: 4,940,548
[45] Date of Patent: Jul. 10, 1990

[54] CHROMATOGRAPHIC SEPARATION PROCESS FOR RECOVERING INDIVIDUAL DIETHYLTOLUENE ISOMERS

[75] Inventor: Hermann A. Zinnen, Evanston, Ill.

[73] Assignee: UOP, Des Plaines, Ill.

[21] Appl. No.: 339,536

[22] Filed: Apr. 17, 1989

[51] Int. Cl.$^5$ .............................................. B01D 15/08
[52] U.S. Cl. .................................. 210/656; 210/674; 210/198.2; 208/310 Z; 585/828
[58] Field of Search .................... 585/828; 208/310 Z; 210/656, 670, 674, 198.2

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,699,182 | 10/1972 | Cattanach | 208/310 Z |
| 3,706,812 | 12/1972 | De Rosset et al. | 260/674 SA |
| 3,723,302 | 3/1973 | Pharis et al. | 208/310 |
| 3,864,416 | 2/1975 | Campbell | 585/828 |
| 3,878,129 | 4/1975 | Rosback | 585/828 |
| 3,894,109 | 7/1975 | Rosback | 585/828 |
| 3,943,184 | 3/1976 | Rosback | 585/828 |
| 4,051,192 | 9/1977 | Neuzil | 585/828 |
| 4,159,284 | 6/1979 | Seko et al. | 585/478 |
| 4,213,913 | 7/1980 | De Rosset | 260/428.5 |
| 4,313,015 | 1/1982 | Broughton | 585/828 |
| 4,402,832 | 9/1983 | Gerhold | 210/659 |
| 4,423,279 | 12/1983 | Kulprathipanja | 585/828 |
| 4,467,126 | 8/1984 | Zinnen | 210/670 |
| 4,482,777 | 11/1984 | Neuzil | 585/828 |
| 4,584,424 | 4/1986 | Barthomeuf | 208/310 Z |
| 4,642,397 | 2/1987 | Zinnen et al. | 568/934 |
| 4,717,778 | 1/1988 | Zinnen | 585/828 |

FOREIGN PATENT DOCUMENTS

| | | | |
|---|---|---|---|
| 51-48620 | 4/1976 | Japan | 585/828 |
| 55-7216 | 1/1980 | Japan | 585/828 |

Primary Examiner—Ernest G. Therkorn
Attorney, Agent, or Firm—Thomas K. McBride; John F. Spears, Jr.; Jack H. Hall

[57] ABSTRACT

A process for separating 3,5-diethyltoluene (3,5-DET) and/or 2,6-diethyltoluene (2,6-DET) from a feed mixture comprising at least one isomer from the group 3,5- and 2,6-diethyltoluene and at least one other isomer thereof, which process comprises contacting the mixture at adsorption conditions with an adsorbent comprising an X zeolite, cation exchanged with a mixture of barium and potassium or sodium, lithium, barium or copper cations or mixtures thereof or a Y zeolite cation exchanged with barium, calcium, sodium, potassium or copper cations or mixtures thereof, thereby selectively adsorbing one or more of said isomers and removing one or more relatively non-adsorbed isomer(s) from contact with the adsorbent. 2,6-diethyltoluene is the most strongly adsorbed isomer with certain adsorbents and is recovered by desorption at desorption conditions with a desorbent material comprising a monocyclic alkyl-substituted aromatic hydrocarbon, e.g., p-diethylbenzene, m-diethylbenzene, p-xylene or p-toluene and optionally, a diluent, e.g., a straight chain or branched paraffin, e.g., n-heptane or iso-octane, an ether or a halogenated hydrocarbon. With certain adsorbents 3,5-DET is the least strongly adsorbed isomer and can be recovered in the raffinate. Certain of the adsorbent-cation combinations perform the dual-function of strongly adsorbing 2,6-DET and least strongly adsorbing 3,5-DET.

28 Claims, 5 Drawing Sheets

CHROMATOGRAPHIC SEPARATION PROCESS FOR RECOVERING INDIVIDUAL DIETHYLTOLUENE ISOMERS

BACKGROUND OF THE INVENTION

1. Field of the Invention

The field of art to which this invention pertains is the solid bed adsorptive separation of isomeric mixtures. More specifically, the invention relates to a process for separating isomers of diethyltoluenes (DET), and particularly, 2,6- and 3,5-diethyltoluene from other diethyltoluene isomers by employing a solid bed adsorption system.

2. Background Information

Both 2,6- and 3,5-diethyltoluene isomers are important starting materials for making diethyltoluene diamines, from which polyureas and polyurethanes are derived. Also, 2,6- and 3,5-diethyltoluene find application as a desorbent material in certain adsorptive chromatographic separations, e.g., p-xylene from its isomers and p-xylene from mixtures of $C_8$ and $C_9$ aromatics.

It is well known in the separation art that certain crystalline aluminosilicates can be used to separate hydrocarbon types from mixtures thereof. Furthermore, X and Y zeolites have been employed in a number of processes to separate individual hydrocarbon isomers. However, no previously published adsorptive chromatographic separation processes have come to light for separating diethyltoluene isomers.

It is, however, known that crystalline aluminosilicates, or zeolites, used in other adsorptive separations of various mixtures, can be in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few ml per hour to many thousands of gallons per hour.

Also, in some cases illustrated herein, it is necessary to remove components of the feed in three product streams in order to remove undesired components of the feed in an intermediate stream from the extract and raffinate streams. This intermediate stream can be termed a second raffinate stream, as in U.S. Pat. No. 4,313,015 or a second extract stream, as in U.S. Pat. No. 3,723,302, both incorporated herein by reference, the latter incorporating abandoned application Ser. No. 100,105 filed Dec. 21, 1970. This case pertains when a contaminating component in the feed is more strongly adsorbed than the desired product or when two product streams are desired and additional material in the feed can be removed in an intermediate stream. In the latter case, if it is desired to keep the concentration of the contaminating component in the product as low as possible, a first extract is taken off, high in concentration of the desired component and lower in the contaminating product followed by a second extract withdrawn at a point in zone 3 between the desorbent inlet and the first extract point, containing a high concentration of the contaminant and a lower concentration of the desired product. It may not be necessary to use a second desorbent if the desorbent is able to first desorb the lightly held product and then desorb the remaining more strongly held contaminants, as disclosed in the aforementioned abandoned application.

Some separations may require a two-stage process, wherein a first stage separation is operated in the rejective mode to obtain a highly purified raffinate product, e.g., 3,5-DET, and the extract from the first stage is reprocessed in the same or a different column with the same adsorbent/desorbent combination to separate the most strongly adsorbed component, the extract product, e.g., 2,6-DET, from the intermediately-held components of the feed. The separations may also be reversed with the first stage separation operation to obtain a highly purified extract product, e.g., 2,6-DET and contacting a second adsorbent with the first stage raffinate in rejective mode to obtain a highly purified second stage raffinate product, e.g., 3,5-DET. The latter modification is similar to that disclosed in deRosset U.S. Pat. No. 4,213,913 and will be understood therefrom.

The invention may also be practiced in a cocurrent, pulsed batch or continuous process, like those described in U.S. Pat. Nos. 4,159,284 and 4,402,832, respectively. The continuous process described in U.S. Pat. No. 4,402,832 is also capable of operating so as to obtain three product streams as mentioned above.

The functions and properties of adsorbents and desorbents in the chromatographic separation of liquid components are well-known, but for reference thereto, Zinnen et al U.S. Pat. No. 4,642,397 is incorporated herein.

Although numerous uses for isomers of DET or mixtures thereof are known, e.g., as precursors of reactants, e.g., curing agents or isocyanates for making polyurethanes, e.g., diethyltoluene diamine and diethyltoluene diisocyanate, they have recently been found to be a highly advantageous "heavy desorbent" for a chromatographic process for separating para-xylene from mixtures of xylene isomers as disclosed in Zinnen application Ser. No. 197,740, filed May 23, 1988, now U.S. Pat. No. 4,864,069. DET isomers are preferred especially for separating xylene mixtures which also contain $C_9$ aromatics, the latter of which are difficult to separate from p-diethylbenzene, (p-DEB) a frequently used desorbent in commercial p-xylene separation processes, e.g., the Parex process of the assignee, UOP.

Currently, mixtures of DET isomers are used in the preparation of polyurethane precursors, but it would be highly desirable to make the precursors from highly pure individual isomers of DET in order to obtain higher yields of the desired reactant. Additionally, the yield of individual DET isomers can be increased by isomerizing, at isomerization conditions, the raffinate isomer mixture with an isomerization catalyst selected for a particular isomer, for example, zeolites containing trace metals, as is known in the art, and recycling the raffinate with increased concentration in one of the isomers with the feed to the instant process.

SUMMARY OF THE INVENTION

In brief summary, the invention is a chromatographic process for separating 2,6-diethyltoluene or 3,5-diethyltoluene from a mixture comprising at least one of 2,6- or 3,5-diethyltoluene and at least one other isomer of diethyltoluene. The process comprises contacting the DET isomer mixture at adsorption conditions with an adsorbent comprising an X-type zeolite, cation exchanged with a sodium, barium, lithium or copper or mixtures thereof, or a mixture of barium and potassium cations or a Y type zeolite, cation exchanged with potassium, barium, calcium, sodium or copper cations or mixtures thereof, thereby selectively adsorbing the 2,6-diethyltoluene thereon and/or retaining the relatively non-adsorbed 3,5-DET in the void volume of the adsorbent and on the relatively non-adsorbing volume thereof and removing, i.e., eluting, 3,5-diethyltoluene from contact with the adsorbent. In the case where 2,6-diethyltoluene is the relatively stronger adsorbed species, the product is recovered by desorption at desorption conditions with a desorbent material comprising monocyclic alkyl-substituted aromatics, e.g., p-xylene, p-diethylbenzene, m-diethylbenzene or toluene.

With an adsorbent, which, in combination with a desorbent liquid mixture, will selectively adsorb all the DET isomers except 3,5-DET, which is relatively non-adsorbed and which elutes near the void volume, 3,5-DET is eluted as raffinate and other components are adsorbed and eluted as extract by desorption with the desorbent. This so-called rejective separation is particularly desirable where the 3,5-DET is the major component, since utilities are lower and adsorbent capacity requirement is lower per unit of output product.

One group of adsorbents, on which 2,6-DET is selectively adsorbed most strongly consists of X type zeolites, exchanged at exchangeable cationic sites with a sodium or copper cation and Y type zeolites, cation exchanged with a barium, calcium, sodium or copper cation. Another group of adsorbents, which least strongly adsorb 3,5-DET, consists of X zeolites, cation exchanged with barium, lithium or a mixture of barium and potassium and Y zeolites, cation exchanged with sodium, calcium, potassium or barium. Among this group of adsorbents, the preferred desorbents, are toluene, p-DEB and p-xylene. A third group of adsorbents, selected from those above, will alter the selectivity pattern such that 2,6-DET is the most strongly adsorbed isomer and 3,5-DET is the least strongly adsorbed, or rejected, isomer. This third group includes Y zeolites, exchanged with barium, sodium or calcium. The preferred desorbents are p-DEB, m-DEB and toluene.

Other embodiments of our invention encompass details about feed mixtures, adsorbents, desorbent materials and operating conditions, all of which are hereinafter disclosed in the following discussion of each of the facets of the present invention.

DETAILED DESCRIPTION OF THE INVENTION

Figure 1:
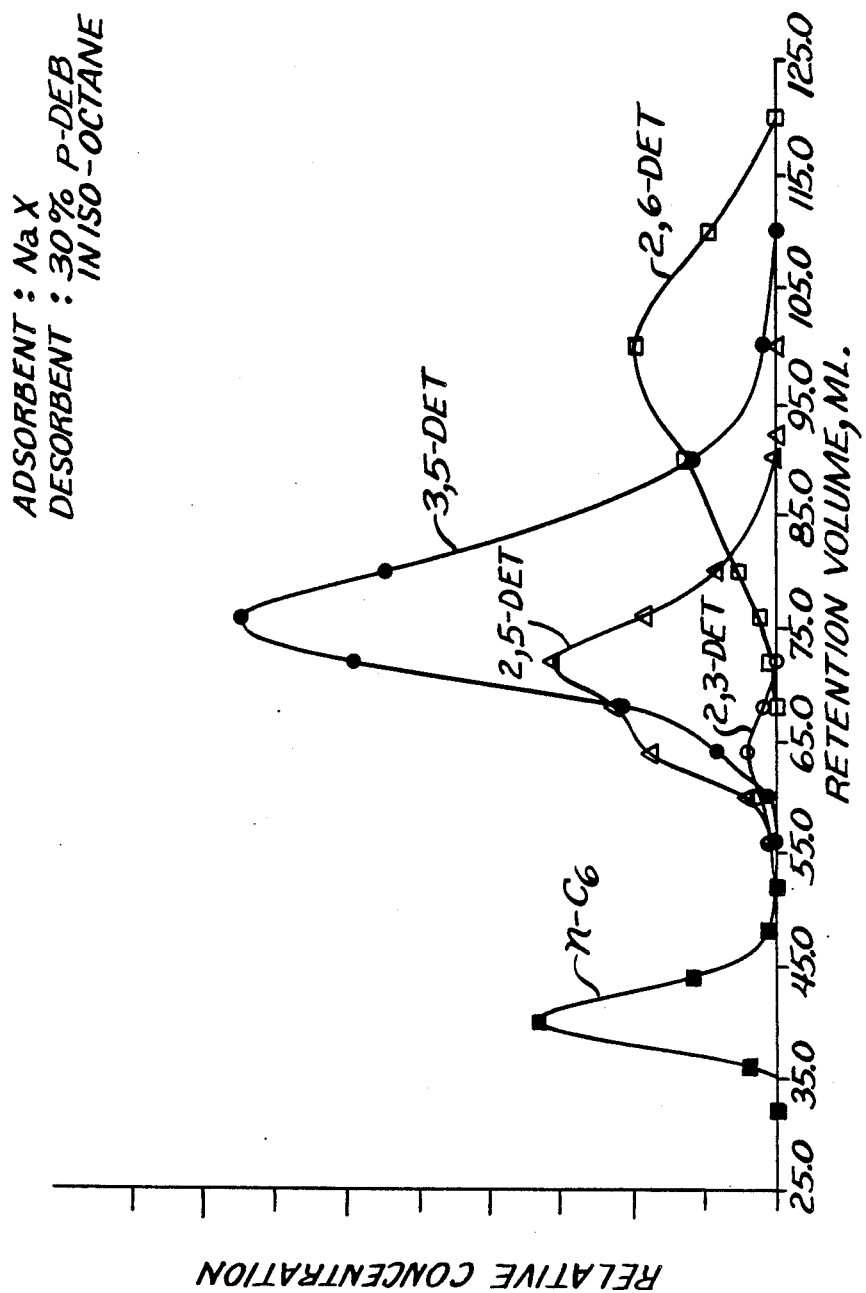
FIG. 1 is a chromatograph trace of the separation of 2,6-diethyltoluene from a mixture of DET isomers with NaX zeolite adsorbent and a desorbent comprising 30% p-diethylbenzene (p-DEB) and 70% isooctane.

Adsorbents to be used in the process of this invention comprise specific crystalline aluminosilicates or molecular sieves, namely, X and Y zeolites. The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves", although widely used, is not strictly suitable since the separation of specific aromatic isomers is apparently dependent on differences in electrochemical attraction between the different isomers and the adsorbent rather than on pure physical size differences between the isomer molecules.

In hydrated form, the crystalline aluminosilicates encompass type X zeolites which are represented by Formula 1 below in terms of moles of oxides:

$$(0.9\pm0.2)M_{2/n}O:Al_2O_3:(2.5\pm0.5)SiO_2:yH_2O \qquad \text{Formula 1}$$

where "M" is a cation having a valence of not more than 3 which balances the electrovalence of the tetrahedra and is generally referred to as an exchangeable cation, "n" represents the valence of the cation, and "y", which represents the moles of water, is a value up to about 9 depending upon the identity of "M" and the degree of hydration of the crystal. As noted from Formula 1, the $SiO_2/Al_2O_3$ mole ratio is $2.5\pm0.5$. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities.

In one embodiment of the invention, in which 3,5-DET is substantially non-adsorbed and recovered as a raffinate product, operative adsorbents are formed when the sodium cation of an X zeolite, as prepared, is substantially completely cation exchanged by barium, lithium or mixtures of barium and potassium. In another embodiment, in which 2,6-DET is selectively adsorbed by the adsorbent, operative adsorbents are formed when the cation of an X zeolite is exchanged with copper or sodium (i.e., original form as prepared).

The type Y structured zeolite, in the hydrated or partially hydrated form, can be similarly represented in terms of moles of oxides as in Formula 2 below:

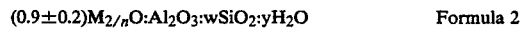

$(0.9 \pm 0.2)M_{2/n}O:Al_2O_3:wSiO_2:yH_2O$    Formula 2 where "M", "n" and "y" are the same as above and "w" is a value greater than about 3 up to about 6. The $SiO_2/Al_2O_3$ mole ratio for type Y structured zeolites can thus be from about 3 to about 6. For both zeolites, the cation "M" may be one or more of a variety of cations but, as the Y type zeolites are initially prepared, the cation "M" is also usually predominately sodium. The type Y zeolite containing predominately sodium cations at the exchangeable cationic sites is, therefore, referred to as a sodium-exchanged type-Y, or NaY, zeolite. Depending upon the purity of the reactants used to make the zeolite, other cations mentioned above may be present, however, as impurities.

In additional embodiments of the invention, 2,6-DET is selectively adsorbed by a Y zeolite exchanged with barium or copper or 3,5-DET can be recovered in a rejective separation with a Y zeolite in the sodium form or exchanged with barium or potassium.

In further embodiments, in which the exchangeable cation sites are exchanged with certain cations, the selectivity order is unexpectedly altered such that 2,6-DET is the most strongly adsorbed DET isomer while 3,5-DET is the rejected, or least strongly adsorbed, DET isomer. In other words, both species can be isolated with a chromatographic process using the same adsorbent and it is further possible to recover both rejected and most strongly adsorbed isomers in a single process. The adsorbents, in which it has been discovered that the selectivity order is as above described, are Y zeolites, cation exchanged with sodium (i.e., in the initial form, or as prepared), calcium or barium cations. In the case of barium-exchanged Y zeolite, the separation of 2,6-DET from the 2,3-DET isomer in the extract is considered somewhat marginal, although operative, but if a feed were used in which little or no 2,3-DET is present, the separation is quite viable. Feed preparation could include either removal of 2,3-DET prior to separation, or isomerization to convert 2,3-DET to another isomer or modification of reaction conditions, e.g., selection of the catalyst, to minimize the formation of 2,3-DET. In some cases, it might be acceptable to produce a 2,6-DET extract containing considerable amounts of 2,3-DET and/or 2,5-DET, for example, as a preferred mixture for use as a desorbent in separating p-xylene from its isomers and ethylbenzene.

Typically, adsorbents used in separative processes contain the crystalline material dispersed in an amorphous matrix or binder, having channels and cavities therein which enable liquid access to the crystalline material. Silica, alumina, clay or mixtures thereof are inorganic substances typical of such matrix materials. Organic materials, such as polymers of styrene/divinylbenzene, are also used as a matrix. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh) (1.9 mm to 250 micron).

Feed mixtures which can be utilized in the process of this invention will comprise at least one of the isomers, 3,5-DET or 2,6-DET, and may additionally contains at least one other $C_{11}$ aromatic isomer. Crude hydrocarbon streams containing substantial quantities of $C_{11}$ aromatic isomers are produced by alkylation and isomerization processes, which are well known to the refining and petrochemical arts. $C_{11}$ aromatics other than DET isomers, such as butyltoluenes and cymenes, may be formed which may necessitate their removal by other means, such as fractionation, or isomerization to DET isomers. Otherwise, they may be coextracted with the product DET isomer or be eluted with the raffinate (non-adsorbed) product, and, of course, reduce the purity of the desired DET isomer product.

To separate the 3,5-DET from a feed mixture containing 3,5-DET and at least one other $C_{11}$ aromatic, the mixture is contacted with an adsorbent, selected from the group aforementioned, on which 3,5-DET is least strongly adsorbed, consisting of X zeolites, cation exchanged with barium, mixtures of barium and potassium or lithium and Y zeolites, cation exchanged with barium, potassium or sodium (i.e., in the original form as prepared), at adsorption conditions whereby the 3,5-DET is the least selectively adsorbed isomer. The other isomers are adsorbed and retained by the adsorbent while the 3,5-DET is relatively unadsorbed and is eluted from the interstitial void spaces between the particles of adsorbent and from the surface of the adsorbent. The adsorbent containing the more selectively adsorbed isomer is referred to as a "rich" adsorbent. The other isomers, which may include 2,6-DET and other DET isomers in the feed are then recovered from the rich adsorbent by contacting the rich adsorbent with a desorbent material at desorption conditions. As aforementioned, the relatively more strongly adsorbed isomers of DET, referred to as the extract, can be isomerized to increase the concentration of one or more of said isomers and can be recycled to the separation process to increase the recovery of 3,5-DET.

The general scheme for such a rejective adsorptive separation is described in copending allowed application Ser. No. 249,538 filed Sept. 26, 1988, incorporated herein by reference. Briefly, the less adsorbed feed component(s) is eluted from the nonselective void volume and weakly adsorbing volume before the more strongly adsorbed component(s); the relatively unadsorbed component(s) is thereby recovered in the raffinate. A particular advantage of such a system lies where the unadsorbed fraction or component is large in relation to the other fraction or components, since substantially less adsorbent and smaller sized equipment is required for a given feed throughout than if the large fraction is selectively adsorbed on the adsorbent.

To separate 2,6-DET from a feed mixture containing 2,6-DET and at least one other $C_{11}$ aromatic, the mixture is contacted with an adsorbent selected from the group mentioned above, on which 2,6-DET is most strongly adsorbed, consisting of X zeolites, cation exchanged with sodium (as prepared) or copper and Y zeolites, cation exchanged with sodium (as prepared), calcium, copper or barium.

In this process, which is generally operated continuously at substantially constant pressures and temperatures to ensure liquid phase, the desorbent material relied upon must be judiciously selected to satisfy several criteria. First, the desorbent material should displace an extract component from the adsorbent with reasonable mass flow rates without itself being so strongly adsorbed as to unduly prevent the extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to the raffinate component or react chemically with the feed components. The desorbent material should additionally be easily separable from the feed mixture that is passed into the process. Both the raffinate components and the extract components are typically removed from the adsorbent in admixture with desorbent material, and without a method of separating at least a portion of desorbent material, the purity of the extract product and the raffinate product would not be very high nor would the desorbent material be available for reuse in the process. It is, therefore, contemplated that any desorbent material used in this process will have a substantially different average boiling point than that of the feed mixture or any of its components, i.e., more than about 5° C. difference, to allow separation of at least a portion of the desorbent material from feed components in the extract and raffinate streams by simple fractional distillation, thereby permitting reuse of desorbent material in the process.

Finally, desorbent materials should be readily available and reasonable in cost. However, a suitable desorbent or desorbents for a particular separation with specific adsorbent are not always predictable. In the preferred isothermal, isobaric, liquid-phase operation of the process of this invention, I have found that desorbent materials comprising monocyclic alkyl-substituted aromatics, such as p-diethylbenzene (p-DEB), m-diethylbenzene (m-DEB), toluene or p-xylene, must be selected with regard to the specific separation in order to effectively desorb the extract from the adsorbent. In well-known manner, the desorbent can be separated from the extract product by distillation. Diluents for the desorbent may also be used in some instances to modify the desorbent strength to achieve better separation, resolution and desorption rates. Examples of such dilution agents include normal paraffins, isoparaffins, ethers, and halogenated hydrocarbons.

Adsorption conditions will include a temperature range of from about 20° to 250° C. with about 60° to about 200° C. being more preferred and a pressure just sufficient to maintain liquid phase, which may be from about atmospheric to 600 psig. Desorption conditions will include the same range of temperatures and pressure as used for adsorption conditions.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation.

A dynamic testing apparatus is employed to test various adsorbents and desorbent material with a particular feed mixture to measure the adsorbent characteristics of adsorptive capacity and exchange rate. The apparatus consists of a helical adsorbent chamber of approximately 70–75 ml volume having inlet and outlet portions at opposite ends of the chamber. The chamber is contained within a temperature control means and, in addition, pressure control equipment is used to operate the chamber at a constant predetermined pressure. Quantitative and qualitative equipment, such as refractometers, polarimeters, chromatographs, etc., can be attached to the outlet line of the chamber and used to analyze, "on-stream", the effluent stream leaving the adsorbent chamber.

A pulse test, performed using this apparatus and the following general procedure, is used to determine data, e.g., selectivities, for various adsorbent systems. The adsorbent in the chamber is filled to equilibrium with a particular desorbent by passing the desorbent material through the adsorbent chamber. At a convenient time, a pulse of feed containing known concentrations of a tracer and of a particular extract component or of a raffinate component, or both, normally diluted in desorbent material is injected for a duration of several minutes. Desorbent flow is resumed, and the tracer and the extract and raffinate components are eluted as in a liquid-solid chromatographic operations. The effluent can be analyzed by on-stream chromatographic equipment and traces of the envelopes of corresponding component peaks developed. Alternatively, effluent samples can be collected periodically and later analyzed separately by gas chromatography.

From information derived from the test, adsorbent performance can be rated in terms of void volume, retention volume for an extract or a raffinate component, and the rate of desorption of an extract component from the adsorbent and selectivity. Void volume is the non-selective volume of the adsorbent, which is expressed by the amount of desorbent pumped during the interval from the initial flow to the center of the peak envelope of the tracer. The net retention volume (NRV) of an extract or a raffinate component may be characterized by the distance between the center of the peak envelope (gross retention volume) of the extract or raffinate component and the center of the peak envelope (void volume) of the tracer component or some other known reference point. It is expressed in terms of the volume in cubic centimeters of desorbent material pumped during this time interval, represented by the distance between the peak envelopes. The rate of exchange or desorption rate of an extract component with the desorbent material can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent material pumped during this time interval. Selectivity, $\beta$, is determined by the ratio of the net retention volumes (NRV) of the more strongly adsorbed component to each of the other components.

The following non-limiting examples are presented to illustrate the process of the present invention and are not intended to unduly restrict the scope of the claims attached hereto.

EXAMPLE 1

The previously described pulse test apparatus was used to obtain data for this example, which illustrates the separation of 2,6-DET, in the extract, from the other isomers of DET. The liquid temperature was 165° and the flow was up the column at the rate of 1.26 ml/min. The feed stream comprised 2.0 ml pulses of a solution containing 1.5 ml of a mixture of the diethyltoluene isomers, 2,3-, 2,5-, 2,6- and 3,5-DET, and 0.3 ml of n-hexane tracer and 1.0 ml of desorbent, 30% vol. p-diethylbenzene in 70% vol. iso-octane. The mixture of DET isomers was approximately 43 % (vol) 3,5-DET, 20% 2,5-DET, 23% 2,6-DET and 7% 2,3-DET with the balance consisting of other $C_{11}$ aromatics. The column was packed with clay bound Na-X faujasite adsorbent of 20–50 mesh particle size. The 2,6-DET isomer was selectively adsorbed and recovered as the extract product.

The selectivity ($\beta$), as earlier described, was calculated from the trace of the peaks generated for the components. The results of this example are shown in the following Table 1 and FIG. 1.

TABLE 1

| Component | NRV (ml) | BETA($\beta$) (ml) |
|---|---|---|
| n-C6 | 0.0 | tracer |
| 2,3-DET | 22.9 | 2.51 |
| 3,5-DET | 36.4 | 1.58 |
| 2,6-DET | 57.4 | reference |
| 2,5-DET | 29.8 | 1.93 |

In general, the above data does show that the present invention provides a 2,6-diethyltoluene selective system, with adequate selectivities for the commercial use of the separation of the present invention.

EXAMPLE 2

The previously described pulse test was also used to obtain data similar to that of Example 1, but using a different adsorbent in place of the NaX zeolite exemplified above. In the first test, the feed was 2.0 ml of a solution containing 1.5 ml of the DET isomer mixture of Example 1, 0.3 ml n-hexane tracer and 1 ml of the same desorbent, 30% p-diethylbenzene in iso-octane. The adsorbent was Cu-X. The column temperature was 165° C., flow rate up the column was 1.14 ml per min. The results of the pulse test, shown in Table 2 below, also indicate a 2,6-DET selective process. In a second test at 145° C. and flow rate of 1.02 cc/min, a feed, comprising 2 cc of a solution containing 1 cc of the same mixture of DET isomers, 1 cc desorbent and 0.3 cc n-C8, was separated in the column filled with Y zeolite exchanged with copper ions in exchangeable sites. The desorbent was 100% diethylbenzene (p-DEB). The results are also shown in the following Table 2.

TABLE 2

| Test No. | Component | NRV (ml) | BETA($\beta$) |
|---|---|---|---|
| 1 | n-C6 | 0.0 | tracer |
|  | 3,5-DET | 28.9 | 1.69 |
|  | 2,3-DET | 26.6 | 1.84 |
|  | 2,6-DET | 48.9 | reference |
|  | 2,5-DET | 26.3 | 1.86 |
| 2 | n-C8 | 0.0 | tracer |
|  | 3,5-DET | 9.7 | 1.71 |
|  | 2,3-DET | 11.7 | 1.42 |
|  | 2,6-DET | 16.6 | reference |
|  | 2,5-DET | 8.7 | 1.90 |

EXAMPLE 3

Further pulse tests were run to demonstrate a process for selectively adsorbing the other isomers of DET in preference to the 3,5-isomer, i.e., the relatively non-adsorbed species, and thereby rejectively separating and recovering 3,5-DET in the raffinate. In the tests, p-DEB or p-xylene was the desorbent, either undiluted or diluted to 30% with either n-heptane, n-dodecane, or iso-octane. Table 3 shows the results of each of the pulse tests in this example. NRV is the net retention volume, discussed previously. For clarity, the $C_{11}$ impurities are not reported.

Figure 2:
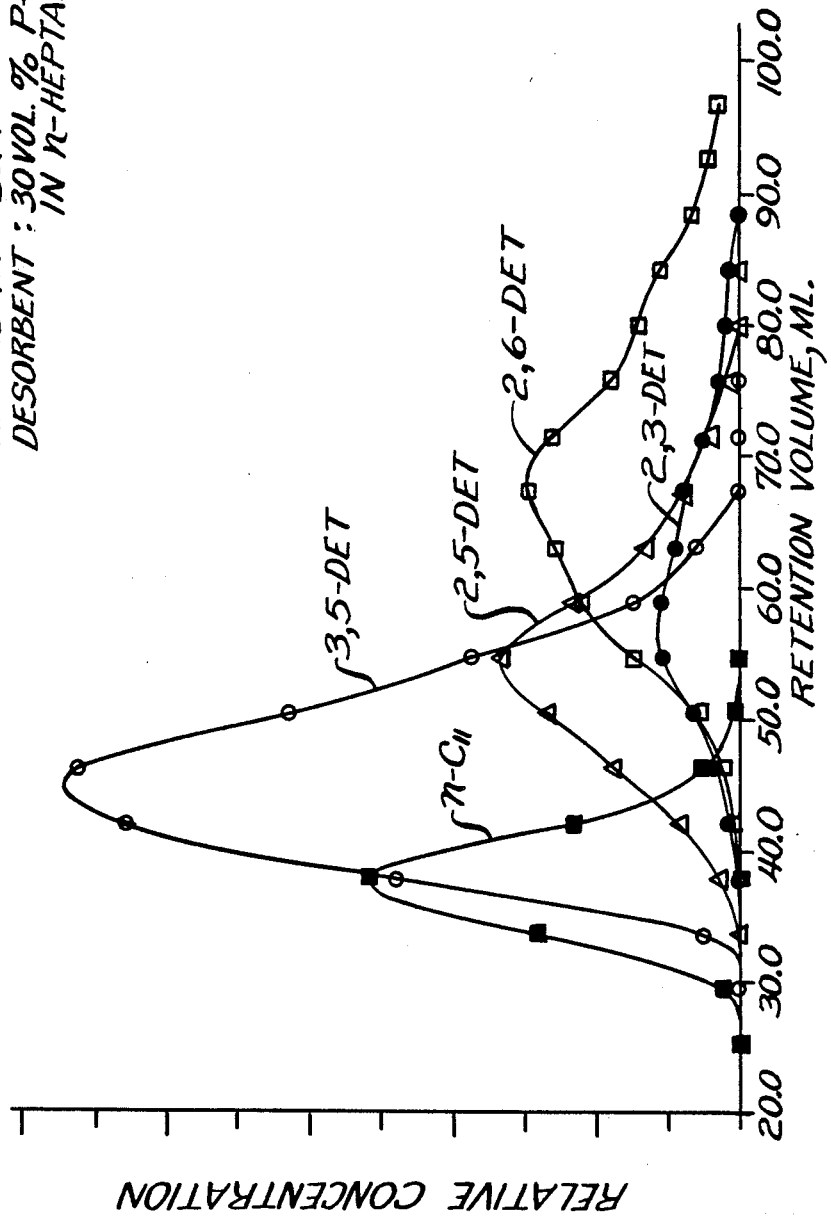
FIG. 2 is a similar chromatographic trace to illustrate the separation of 3,5-DET by a rejective separation process, using a BaY adsorbent and 30 vol. % p-DEB/70 vol. % n-heptane desorbent. This figure also illustrates an embodiment of the invention in which 2,6-DET is the most strongly adsorbed isomer, therefore permitting recovery of 3,5-DET and 2,6-DET in purified form in the same process.
Figure 3:
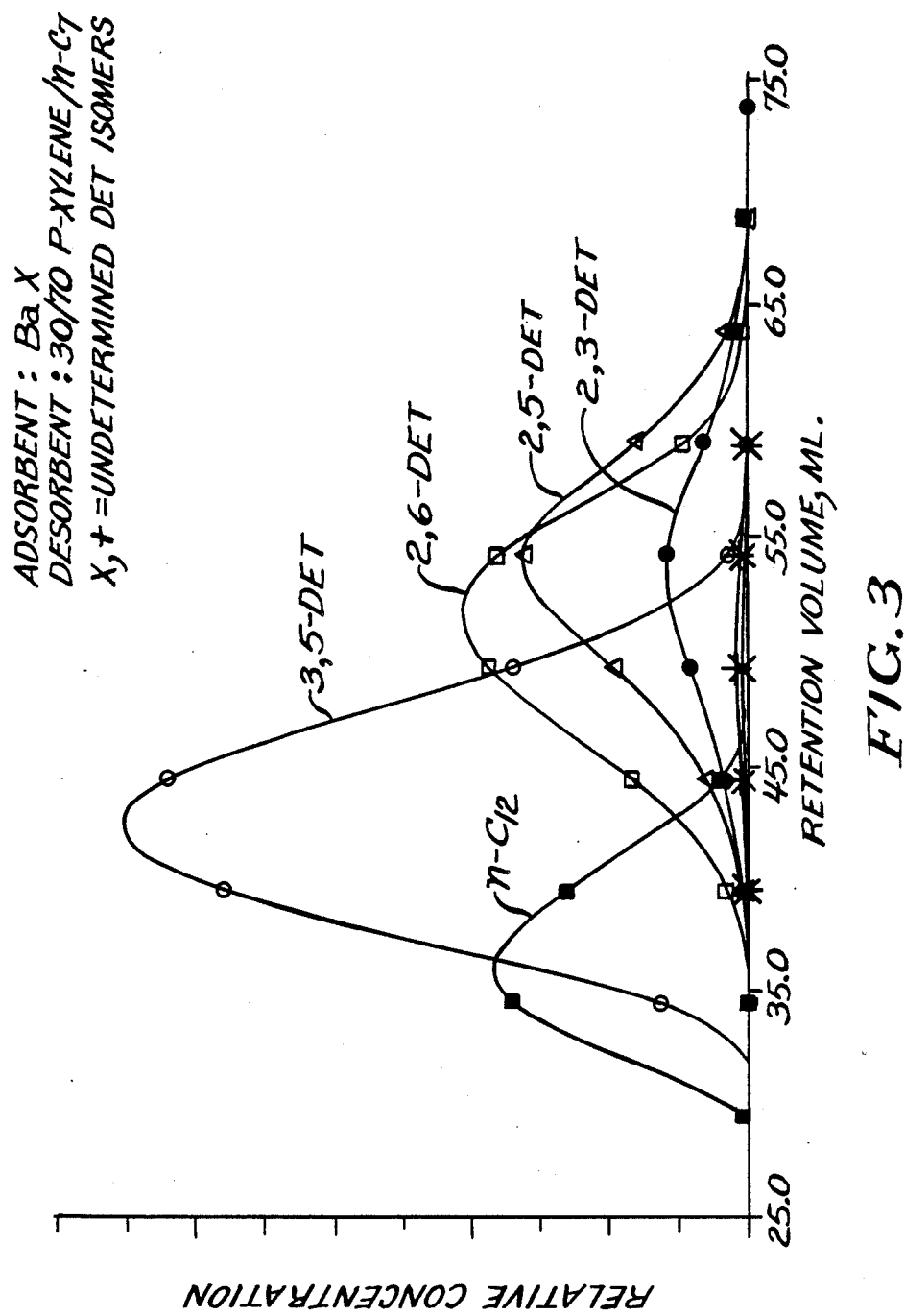
FIG. 3 is a chromatographic trace to illustrate the separation of 3,5-DET by a rejective separation process using a Ba-exchanged X faujasite adsorbent and a mixture of 30% p-xylene and 70% n-heptane as desorbent.

In Test No. 1, the adsorbent was a Y zeolite, exchanged with barium ions at the exchangeable sites and the desorbent was 30% p-DEB diluted with n-heptane. The feed pulse was 2 ml of a solution containing 1.7 ml of the DET isomer mixture of Example 1 and 0.3 ml n-$C_{11}$ tracer. The results of the pulse test are shown in FIG. 2 and Table 3 below. As can also be seen in FIG. 2, 2,6-DET was most strongly adsorbed onto the BaY zeolite and therefore illustrates one adsorbent which can be employed to separate either or both 2,6- and 3,5-DET isomers in a single process. In Test No. 2, the adsorbent was X zeolite exchanged with a mixture of barium and potassium ions and the desorbent was 30% p-DEB in n-heptane. The feed pulse was the same as in Test No. 1. In Test No. 3, the adsorbent was X zeolite, exchanged with lithium ions and the desorbent was 30% p-DEB in iso-octane. The feed pulse was the same as in Example 1. In Test No. 4, the adsorbent was Y zeolite exchanged with barium at the exchangeable sites and the desorbent was 30% toluene in n-heptane. The feed pulse was the same as in Test No. 1. In Test No. 5, the adsorbent was KY and the desorbent was 30% p-xylene in n-heptane. The feed pulse was 5 cc of a solution containing 1.5 cc of the DET isomer mixture of Example 1, 0.29 cc n-$C_9$ tracer, and 3 cc desorbent. In Test No. 6, the adsorbent was X faujasite, exchanged with barium cations, and the desorbent was 30% p-xylene in n-heptane. The feed pulse was 2 cc of a solution containing 1.7 cc of the DET isomer mixture of Example 1 and 0.3 cc n-$C_{12}$. As can be seen in FIG. 3, 3,5-DET was the least strongly adsorbed isomer, illustrating a separating system which can be employed to separate 3,5-DET in a rejective process.

TABLE 3

| Test No. | Component | NRV (ml) | BETA($\beta$) |
|---|---|---|---|
| 1 | n-C11 | 0.0 | tracer |
| BaY | 3,5-DET | 8.0 | 3.69 |
| Temp: 120° C. | 2,3-DET | 22.6 | 1.30 |
| Flow Rate: | 2,6-DET | 29.4 | 1.00 |
| 1.26 cc/min | 2,5-DET | 16.2 | 1.81 |
| 2 | n-C11 | 0.0 | tracer |
| BaKX | 3,5-DET | 3.9 | reference |
| Temp: 145° C. | 2,3-DET | 5.8 | 0.67 |
| Flow Rate: | 2,6-DET | 7.0 | 0.56 |
| 1.32 cc/min | 2,5-DET | 8.5 | 0.46 |
| 3 | n-C6 | 0.0 | tracer |
| LiX | 3,5-DET | 30.2 | reference |
| Temp: 165° C. | 2,3-DET | 51.5 | 0.59 |
| Flow Rate: | 2,6-DET | 49.6 | 0.61 |
| 1.17 cc/min | 2,5-DET | 34.0 | 0.89 |

TABLE 3-continued

| Test No. | Component | NRV (ml) | BETA($\beta$) |
|---|---|---|---|
| 4 | n-C11 | 0.0 | tracer |
| BaY | 3,5-DET | 3.1 | reference |
| Temp: 125° C. | 2,3-DET | 15.9 | 0.19 |
| Flow Rate: | 2,6-DET | 15.2 | 0.20 |
| 1.02 cc/min | 2,5-DET | 12.8 | 0.24 |
| 5 | n-Nonane | 0.0 | tracer |
| KY | 3,5-DET | 20.6 | reference |
| Temp: 150° C. | 2,3-DET | 26.6 | 0.77 |
| Flow Rate: | 2,6-DET | 28.1 | 0.73 |
| 1.22 cc/min | 2,5-DET | 29.8 | 0.69 |
| 6 | n-C12 | 0.0 | tracer |
| BaX | 3,5 DET | 5.9 | reference |
| Temp: 200° C. | 2,3-DET | 16.5 | 0.36 |
| Flow Rate: | 2,6-DET | 14.4 | 0.41 |
| 1.23 cc/min | 2,5-DET | 16.9 | 0.35 |
|  | DET* | 12.7 | 0.46 |
|  | DET* | 12.1 | 0.49 |

*Undetermined isomer

EXAMPLE 4

Figure 4:
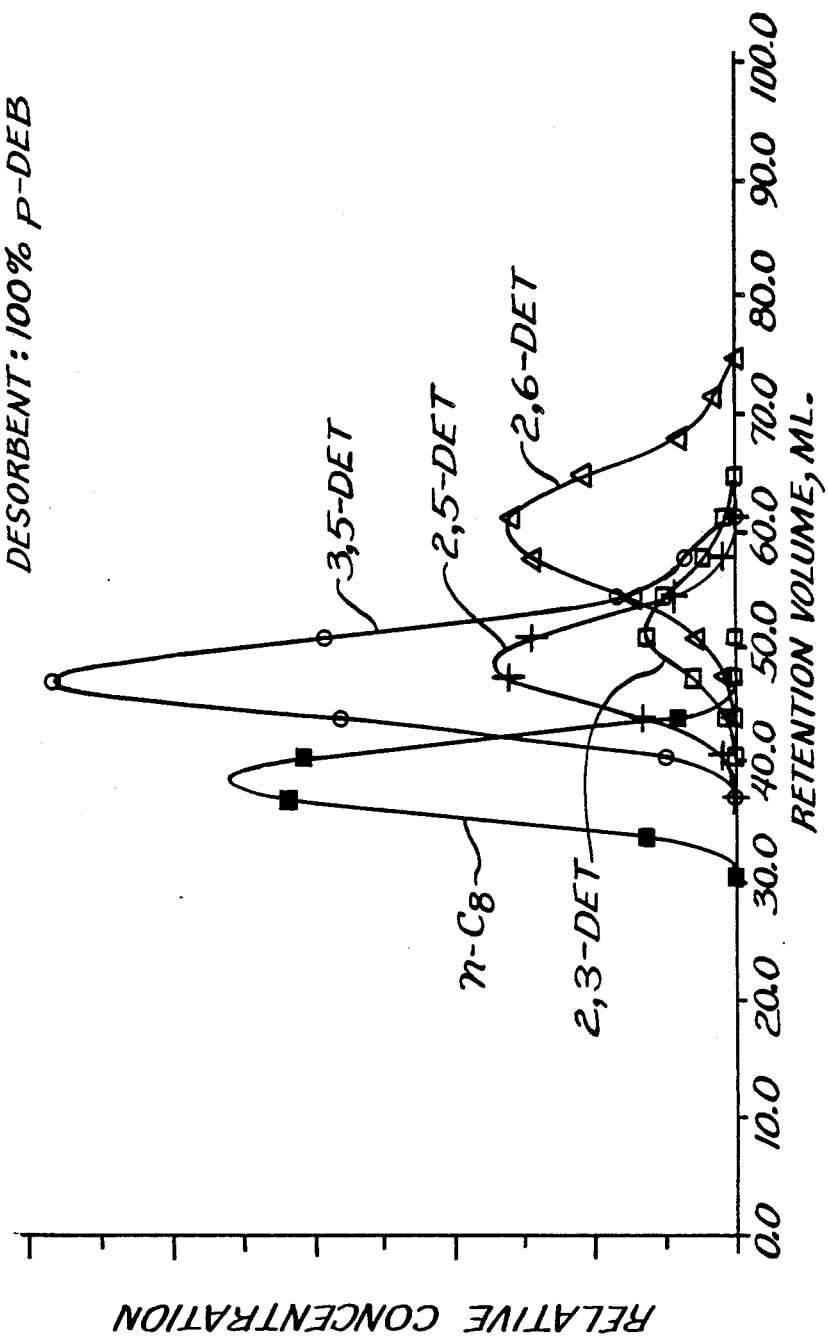
FIGS. 4 and 5 are chromatographic traces similar to FIG. 2 in that both 2,6-DET and 3,5-DET can be separated and separately recovered in the extract and raffinate, respectively, in FIG. 4 with a NaY zeolite adsorbent and p-DEB desorbent and in FIG. 5 with a CaY zeolite adsorbent and 30% m-DEB in n-heptane as desorbent.
Figure 5:
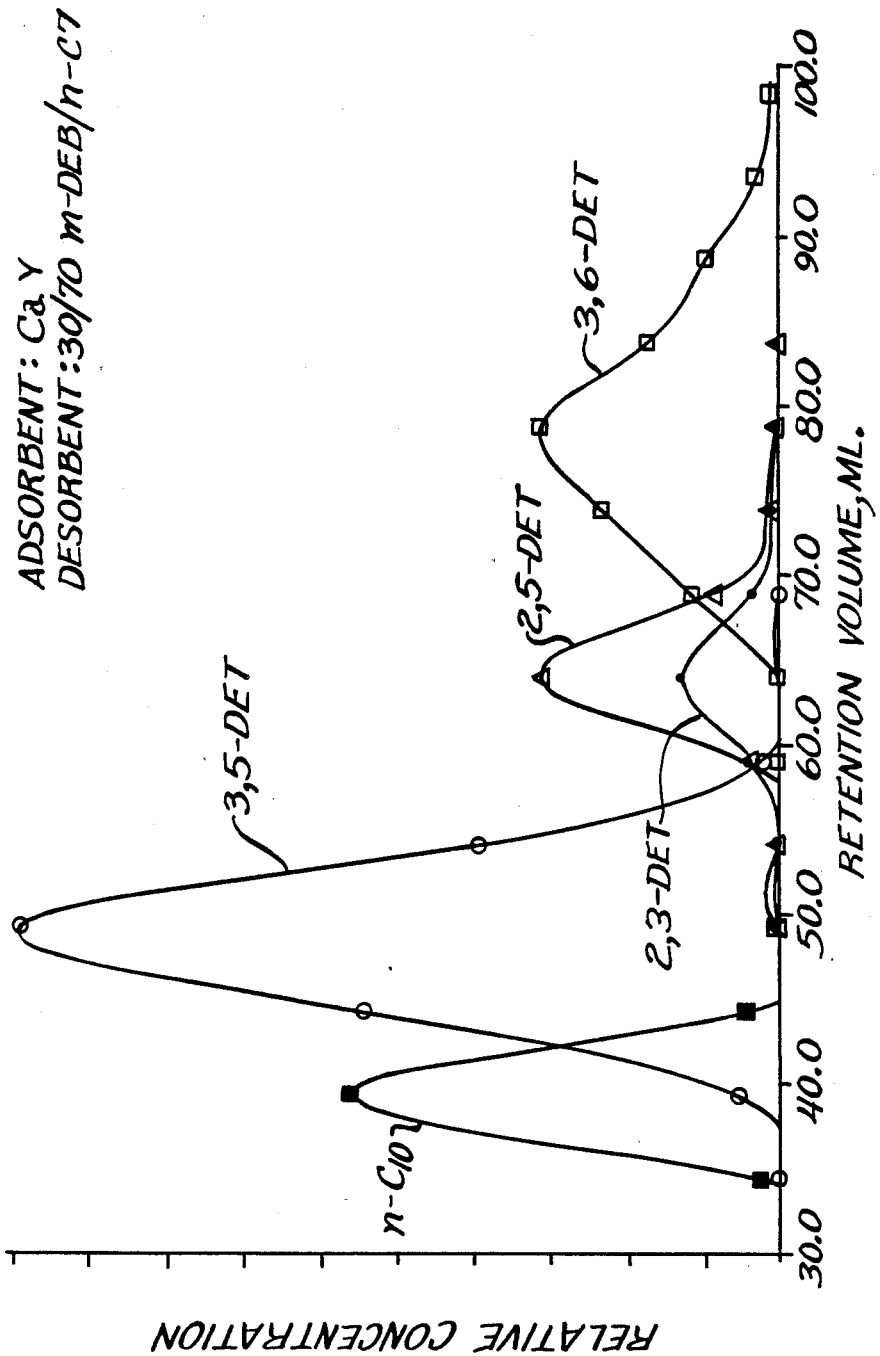

Further pulse tests were run to demonstrate an additional adsorbent whereby 2,6-DET and 3,5-DET can be recovered as the extract product and/or the raffinate product, respectively, in a single stage, if desired, or in a two-stage process, as aforementioned. In a single stage, a third, intermediate product stream is required, but both isomers can be separately recovered in purified form in a two-stage process, where the 2,6-DET extract is the product in the first stage and the raffinate, 3,5-DET, is the product in the second stage, which is a rejective process as described above. The adsorbent and desorbent can be the same in both stages, resulting in lower capital costs, or a different combination may be used. Also, the sequence of the stages, as set forth above, can be reversed. In Test No. 1, the feed pulse was 2 cc of a solution containing 1 cc of the DET isomer mixture of Example 1, 1 cc of the desorbent and 0.3 cc n-C8. The desorbent was 100% p-DEB. In Test No. 2, the feed pulse was 5 cc of a solution containing 1 cc desorbent, 0.3 cc n-C10 tracer, and 4 cc of a DET isomer mixture with the following composition: 41.2 vol % 3,5-DET, 5.4% 2,3-DET, 14.3% 2,6-DET, and 9.2% 2,5-DET, with the balance consisting of other C11 aromatics such as butyl toluene isomers and p-cymene. The desorbent in this test was 50% p-DEB in n-heptane. In Test No. 3, at 200° C. and column flow of 1.21 cc/min, the feed pulse was 2 cc of the same solution as Test 1. The desorbent was 30% m-diethylbenzene (m-DEB) diluent with n-heptane. The adsorbent in each of the preceding tests was Y zeolite, with sodium ions in the cation-exchangeable sites. In Test No. 4, at 200° C. and column flow rate of 1.23 cc/min., the feed pulse was 2 cc of the same solution as Test 1. The adsorbent in this test was Y zeolite with calcium ions in the cation-exchangeable sites. The desorbent in this test was 30% m-DEB in n-heptane. The results of the experiments are shown in Table 4 below. Pulse Test No. 1 is illustrated in the chromatograph of FIG. 4; Pulse Test No. 4 is illustrated in the chromatograph of FIG. 5. It is noted from Test No. 2 that even in the presence of C11 impurities such as p-cymene and butyltoluenes, 2,6-DET and 3,5-DET can be recovered in purified form, since they are the most strongly adsorbed and least strongly adsorbed species, respectively.

TABLE 4

| Test No. | Component | NRV (ml) | BETA($\beta$) |
|---|---|---|---|
| 1 | n-C8 | 0.0 | tracer |
| Temp: 145° C. | 3,5-DET | 8.7 | 2.46 |
| Flow Rate: | 2,3-DET | 13.3 | 1.6 |
| 1.02 cc/min | 2,6-DET | 21.4 | reference |
|  | 2,5-DET | 9.9 | 2.16 |
| 2 | n-C10 | 0.0 | tracer |
| Temp: 150° C. | 3,5-DET | 8.1 | 3.99 |
| Flow Rate: | p-cymene | 16.5 | 1.75 |
| 1.26 cc/min | 2,3-DET | 17.6 | 1.64 |
|  | 2,6-DET | 28.8 | reference |
|  | 2,5-DET | 14.2 | 2.02 |
|  | butyl toluene isomer | 19.3 | 1.49 |
|  | butyl toluene isomer | 14.2 | 2.03 |
| 3 | n-C10 | 0.0 | tracer |
| Temp: 200° C. | 3,5-DET | 9.4 | 3.21 |
| Flow rate: | 2,5-DET | 19.4 | 1.56 |
| 1.21 cc/min | 2,3-DET | 20.5 | 1.47 |
|  | 2,6-DET | 30.2 | reference |
| 4 | n-C10 | 0.0 | tracer |
| Temp: 200° C. | 3,5-DET | 9.1 | 4.19 |
| Flow Rate: | 2,3-DET | 24.5 | 1.56 |
| 1.23 cc/min | 2,5-DET | 24.9 | 1.54 |
|  | 2,6-DET | 38.2 | reference |

What is claimed:

1. A process for separating isomers of diethyltoluene from a feed mixture thereof, said feed mixture comprising at least one isomer from the group 2,6-diethyltoluene and 3,5-diethyltoluene and at least one other isomer of diethyltoluene said process comprising contacting said feed mixture at adsorption conditions with an adsorbent selected from the group consisting of X type zeolites, cation exchanged with barium and potassium cations or a sodium, lithium, or copper cation or mixtures thereof and Y type zeolites cation exchanged with barium, calcium, sodium, potassium or copper cations or mixtures thereof, thereby selectively adsorbing one of said isomers, removing at least one relatively non-adsorbed isomer from contact with said adsorbent and recovering said adsorbed isomer by desorption, at desorption conditions, with a desorbent material comprising monocyclic alkyl substituted aromatics.

2. The process of claim 1 wherein said adsorbent is selected from the group consisting of X type zeolites, cation exchanged with a sodium, or copper cation and Y type zeolites, cation exchanged with a barium, calcium, sodium or copper cation, said desorbent is selected from the group consisting of p-diethylbenzene, m-diethylbenzene, p-xylene and toluene, said adsorbed isomer is 2,6-diethyltoluene and 2,6-diethyltoluene is recovered as extract product.

3. The process of claim 2 wherein said desorbent material additionally comprises a diluent.

4. The process of claim 1 wherein said non-adsorbed isomer is 3,5-diethyltoluene and 3,5-diethyltoluene is recovered as raffinate product.

5. The process of claim 4 wherein said adsorbent is selected from the group consisting of X zeolites, cation exchanged with a mixture of barium and potassium or lithium and Y zeolites, cation exchanged with sodium, calcium, potassium or barium.

6. The process of claim 5 wherein said desorbent is selected from the group consisting of toluene, p-diethylbenzene and p-xylene.

7. The process of claim 6 wherein said desorbent material additionally comprises a diluent.

8. The process of claim 4 wherein said adsorbent is Na-Y, and said desorbent comprises p-diethylbenzene, and said adsorbed isomer is 2,6-diethyltoluene and 2,6-diethyltoluene is recovered as extract product.

9. The process of claim 8 wherein said desorbent material additionally comprises a diluent.

10. The process of claim 9 wherein said diluent comprises normal paraffins, isoparaffins, ethers and halogenated hydrocarbons.

11. The process of claim 8 wherein said desorbent material additionally comprises a diluent.

12. The process of claim 4 wherein said adsorbent is BaY, and said desorbent comprises p-diethylbenzene or toluene, said adsorbed isomer is 2,6-diethylbenzene and 2,6-diethyltoluene is recovered as extract product.

13. The process of claim 12 wherein said desorbent material additionally comprises a diluent.

14. The process of claim 4 wherein said adsorbent is CaY and said desorbent comprises m-diethylbenzene, said adsorbed isomer is 2,6-diethylbenzene and 2,6-diethyltoluene is recovered as extract product.

15. The process of claim 14, wherein said desorbent material additionally comprises a diluent.

16. The process of claim 4 wherein said desorbent is selected from the group consisting of p-diethylbenzene, m-diethylbenzene, p-xylene and toluene.

17. The process of claim 16 wherein said desorbent additionally comprises a diluent.

18. The process of claim 1 wherein said desorbent is selected from the group consisting of toluene, p-diethylbenzene, m-diethylbenzene and p-xylene.

19. The process of claim 18 wherein said desorbent additionally comprises a diluent.

20. The process of claim 1 wherein said adsorption and desorption conditions include a temperature within the range of from about 20° C. to about 200° C. and a pressure sufficient to maintain liquid phase.

21. The process of claim 1 wherein said process is effected with a simulated moving bed flow system.

22. The process of claim 1 wherein said process is effected with a fixed bed system.

23. A process for separating 3,5-diethyltoluene from a feed mixture comprising 3,5-diethyltoluene and at least one isomer thereof, said process comprising contacting said feed mixture at adsorption conditions with an adsorbent selected from the group consisting of X type zeolites, cation exchanged with a mixture of barium and potassium cations or lithium cations and Y type zeolites, cation exchanged with barium, calcium, potassium or sodium cations, thereby selectively adsorbing said isomers of 3,5-diethyltoluene and recovering, as raffinate, relatively non-adsorbed 3,5-diethyltoluene from said adsorbent.

24. The process of claim 23 wherein said selectively adsorbed isomers of 3,5-diethyltoluene are recovered by desorption at desorption conditions with a desorbent material comprising p-diethylbenzene, m-diethylbenzene, p-xylene or toluene.

25. The process of claim 23 wherein said feed mixture contains 2,6-diethyltoluene and said 2,6-diethyltoluene is recovered in substantially greater purity by said desorption.

26. A process for separating 2,6-diethyltoluene from a feed mixture comprising 2,6-diethyltoluene and at least one isomer thereof, said process comprising contacting said mixture at adsorption conditions with an adsorbent selected from the group consisting of X type zeolites, cation exchanged with sodium or copper cations and Y type zeolites, cation exchanged with sodium, barium, calcium or copper cations, thereby selectively adsorbing said 2,6-diethyltoluene, removing the remainder of said mixture from said adsorbent, and then recovering said 2,6-diethyltoluene by desorption at desorption conditions with a desorbent material comprising a monocyclic alkyl-substituted aromatic hydrocarbon.

27. The process of claim 26 wherein said adsorption and desorption conditions include a temperature within the range of from about 20° C. to about 200° C. and a pressure sufficient to maintain liquid phase.

28. The process of claim 26 wherein said hydrocarbon is selected from the group consisting of p-diethylbenzene, m-diethylbenzene, p-xylene and toluene.

* * * * *